US00PP13059P2

(12) United States Plant Patent
Brown

(10) Patent No.: US PP13,059 P2
(45) Date of Patent: Oct. 8, 2002

(54) *CYNODON DACTYLON* PLANT NAMED 'PLATEAU'

(75) Inventor: Peter Brown, Collaroy Plateau (AU)

(73) Assignee: Triodia Pty. Limited, New South Wales (AU)

( * ) Notice: Subject to any disclaimer, the term of this patent is extended or adjusted under 35 U.S.C. 154(b) by 0 days.

(21) Appl. No.: 09/679,112

(22) Filed: Oct. 4, 2000

(51) Int. Cl.[7] ..... A01H 5/00
(52) U.S. Cl. ..... Plt./389
(58) Field of Search ..... Plt./389

(56) References Cited

PUBLICATIONS

UPOV–ROM GTITM Computer Database 2000/05, GTI JOUVE Retrieval Software, citation(s) for 'Plateau' Oct. 10, 2000.*

* cited by examiner

*Primary Examiner*—Bruce R. Campell
*Assistant Examiner*—Annette H. Para
(74) *Attorney, Agent, or Firm*—Christie, Parker & Hale, LLP

(57) ABSTRACT

The new variety comprises a *Cynodon dactylon* plant named 'Plateau' exhibiting a low growing height and prostrate spreading habit making it suitable for wide landscape usage.

2 Drawing Sheets

BACKGROUND OF THE INVENTION

The present invention relates to a new and distinct *Cynodon dactylon* variety.

The new variety is the result of a spontaneous mutation of a common, unnamed, and unpatented couch grass (*Cynodon dactylon*) growing on the property of the inventor at Collaroy Plateau, New South Wales, Australia. The new variety was propagated vegetatively through four generations. The varietal denomination of the new variety is 'Plateau'.

There is an ongoing need worldwide, and in particular in the United States of America, for turf grass varieties which are hard wearing, low in maintenance, which provide good ground cover, are of low growing height with a prostrate spreading habit, high sward density, medium to low seed head production and lustrous coloration. Such varieties find particular use on golf courses, bowling greens, parks, playing fields, as well as in domestic and commercial settings.

The parent of 'Plateau', an unnamed couch grass seedling, is a representative example of generic couch grass widely grown and used in domestic lawns, in golf courses, and in parks. As described hereinafter 'Plateau' is an advantageous turf grass species in many respects over and above commercial grass species, and common unnamed which grass is represented by the parent.

SUMMARY OF THE INVENTION

The new variety of *Cynodon dactylon,* 'Plateau', exhibits low growing height, prostrate spreading habit, prostrate shoot growth, short internode length, high sward density, wide stolon to rhizome width ratio, and medium seed head frequency, amongst other characteristics herein described which distinguish the subject variety from presently available commercial turf grass varieties.

Under wide climatic conditions, for example, in coastal areas of California, inland areas and in temperate and less temperate conditions, green color quality, and good cover/sword density can be maintained throughout the year. The new variety is vegetatively propagated from sod, plugs, tillers or stolons and rhizome pieces. Asexual propagation by rhizome and tillers in various commercial growing trials in Narrabeen, New South Wales, Australia has demonstrated that the combination of characteristics of the new variety are transmitted through successive propagations.

The most similar variety known to the inventor is the variety 'Riley's Super Sport', the subject of U.S. Plant Pat. No. 1,181 issued Jan. 18, 2000 which forms a dense turf of low growing height. Another comparator is the variety 'Greenlees Park' which is a widely available commercial variety of the same species and which is the parent of 'Riley's Super Sport'. 'Plateau' differs from 'Riley's Super Sport' in that it has less frequent nodes, medium to low seed head frequency, longer leaves, narrower stolons and thicker rhizomes. 'Plateau' differs from 'Greenlees Park' in that is has a low growing height, prostrate shoot growth, shorter internode length, high sward density, wide stolon to rhizome width ratio, and medium to low seed head frequency.

BRIEF DESCRIPTION OF ILLUSTRATIONS

The accompanying illustrations show typical specimens of the vegetative growth of the new variety.

FIG. 1 shows a close up of a turf section and of isolated stolons of the new variety with comparative varieties 'Riley's Super Sport' and 'Greenlees Park', showing growth habit/turf appearance, node frequency and stolon thickness.

FIG. 2 shows a replicated lateral extension rate trial, with plugs of 'Plateau' (P), 'Riley's Super Sport' (R) and 'Greenlees Park' (GP) spaced in repeated sequence (4) along the plot, twenty-one days after planting. Long radiating stolons of 'Plateau' are clearly evident.

DESCRIPTION OF THE NEW VARIETY

The description of color is by reference to The Royal Horticultural Society Colour Chart. The plants described are about 13 months old.

The new variety has a prostrate (to 50 mm) spreading growth habit with a rapid lateral extension rate (about 20 cm in twenty one days) and high node density.

Leaf blades are of green coloration (near 147A), the leaf length is short, having a mean length of about 20.8 mm, the leaf width is narrow, having a mean width of about 2.3 mm, and the mean leaf length:width ratio is about 9.1:1. The ligule has a dense row of short hairs about 0.2 to 0.5 mm long on a membranous rim with longer hairs about 1.0 to 1.5 mm long at each end. The blades are flat linear-triangular about 2.0 to 2.5 mm long, about 1.- to 2.0 mm wide, pointed, glabrous and sparsely pubescent, minutely scabrous on the margin. Auricles are absent and vernation conduplicate. The sheath is glabrous and sparsely pubescent.

Stolons of 'Plateau' are red/purple (near 60C). They are of high density, with a short internode length having a mean of node frequency of about 5 per cm length. Stolons are of medium thickness, having a mean thickness of about 1.06 mm. Stolons are strongly prostrate, and generally form about 30 to 50 mm long.

The new variety is strongly rhizomatious with a mean width of about 1.9 mm, and a narrow stolon to rhizome thickness ratio having a mean of about 1.8 mm.

Culms are smooth, slender decumbent to semi-erect, about 20 to 50 mm long, about 1.0 to 2.0 mm wide, and colored red/purple (near 60C).

Inflorescence of the new variety is digitate of 2 to 7 spikes, linear about 15 to 30 mm long and about 1.0 to 1.5 mm wide; spikelets broad, laterally compressed to about 3.0 mm long and about 2.0 mm wide; glumes acuminate about 1.0 to 2.5 mm long; lemma keeled, mucronate about 1.5 to 3.0 mm long, ciliolate along the keel; sterile rachilla extension 0.5 to 1.5 mm long, sometimes topped with a vestigial spikelet, and the anther color is red/purple (near 74D).

Seed head frequency of the new variety is low to medium having a mean of about 9.2 per 100 $cm^2$.

Winter growth of 'Plateau' is comparable with other known *Cynodon dactylon* varieties.

The new variety is vegetatively propagated from sod, plugs or stolon or rhizome pieces, as mentioned presiously. It performs best in sun, but also grows well in shade. The variety has an easily controllable mat density, and is hard wearing. As a consequence, the variety is responsive to mowing management in order to provide, for example, a firm surface for use such as in bowling greens and golf tees, or a soft surface for use such as in parks, in domestic situations, or on golf fairways.

Under conditions of very limited water availability, the new variety revives quickly on the application of water.

The turf formed from the new variety is accordingly suitable for situations requiring a durable, high quality lawn or turf that is tolerant to heat and drought stress. As mentioned previously, such applications include bowling greens, sport stadia, golf courses, parks, public planting areas and domestic lawns.

In general, *Cynodon dactylon* 'Plateau' has been observed to be no more susceptible to pests and diseases than other commercial varieties. In particular, 'Plateau' has been observed to display delayed susceptibility to the fungal disease syndrome of 'Helminthosporium' (Bipolaris and Dreschlera spp.). Fungal diseases of this nature are influenced by climatic conditions and are not usually persistent. 'Dollar Spot' (Lanzia spp. and others) and 'Spring Dead Spot' (*Leptosphaeria namari* and *L. korrea*) have not been observed on 'Plateau' and may indicate strong resistance to these diseases.

Common pests of *Cynodon dactylon* species such as scarab beetles, grass-eating caterpillars, mites, flea beetle and tip maggot has been observed on 'Plateau'. The subsequent plant injury and susceptibility observed is no greater in comparison to that on other varieties of *Cynodon dactylon.*

The accompanying illustration serves to show the distinctive features of the new variety. As can be seen from FIG. 1 the new variety has a prostrate growth habit which can be finely cut, such as to about 2 to 3 mm height, thus allowing a dense mat of prostrate growth habit for use as a putting green, bowling surface or other such surface, or the variety may be cut at a greater height to provide a durable traffic surface, such as a golf fairway, verge of a bowling green and many other such applications. FIG. 1 shows the high node frequency, as depicted by short internode length, long spreading stolons. The new variety is a low lying grass and contrasts with the marked vertical extension of the comparative variety 'Greenlees Park'. The new variety is clearly distinguished from the comparative varieties 'Riley's Super Sport' on the basis of the internode length, longer leaf length and long spreading stolons. The new variety is clearly distinguished from the comparative variety 'Greenlees Park' on the basis of greater node frequency, shorter leaf length, prostrate spreading growth habit, and dense growth habit. The principal features of prostrate and dense habit, long spreading stolons and short internode length are clearly observable.

To further illustrate the differences between the new variety 'Plateau' and the comparative varieties 'Riley's Super Sport' and 'Greenlees Park', tests were conducted at the Narrabeen, New South Wales, Australia, RSL Bowling Green trial site in the summer of 1998/1999. Twelve plots measuring 2×1 m were planted in the field in loamy sand of uniform texture, using four replicates of the new variety 'Plateau', and the two comparator varieties 'Riley's Super Sport' and 'Greenlees Park'. This plot order was replicated four times. One hundred stolons were used to establish individual trial plot replicates.

Irrigation and fertilisation was carried out as required at standard rates. Irrigation of the trial plots was by daily hand watering in the initial two weeks of grass establishment. Following this the plots were watered twice per week to soil field capacity using perforated, detachable above ground aluminum pipes (Perf-O-Rain). Irrigation was suspended at times when rainfall was sufficient to sustain development of the grasses.

All fertilization was by controlled release fertilizer applied at the rate of 70 grams/$m^2$ to provide 8.6 grams elemental nitrogen per square meter, 4.13 grams elemental phosphorous per square meter, and 7.42 grams elemental potassium per square meter. Four applications of this fertilizer were made at this rate during the trial period. These were in January, March, and November 1998 and in February 1999.

Two insecticide treatments were applied in the growing season. Insecticide treatments were as follows: February and April 1998, Chlopyrofos at 7 ml per 100 $m^2$ to control grass eating caterpillars; December 1998, "Rogor" as dimethoate at 4 mg per 100 $m^2$ to control Bermuda (Couch) grass tip maggot; and February 1999, "Dursban" as chlorpyrofos at 7 mg per 100 $m^2$ to control grass eating caterpillars.

No mowing was carried out. Measurements were taken from 100 random samples for unmown height, leaf length and width, node frequency, twenty five samples for rhizome/stolon thickness, angle of shoot emergence and twelve samples were taken for group counts for seed head density. The results of these comparative test evaluations are shown in Table 1. Also shown in Table 1 and depicted in FIG. 2 is a lateral extension rate trial of four repeated spaced replicates of 'Plateau', 'Riley's Super Sport' and 'Greenlees Park'.

Statistical differences among the cultivars were determined according to standard statistical tests.

'Plateau' has a prostrate spreading habit compared with the very prostrate habit of 'Riley's Super Sport' and the vertical growth habit of 'Greenlees Park'. Node density of 'Plateau' was high, having a mean node frequency (number/cm) of 5.03, compared with 6.6. for 'Riley's Super Sport' and 4.30 for 'Greenlees Park'. High node density of the new variety, combined with long leaf length and thin stolon width, compared to the comparative variety 'Riley's Super Sport' results in a high density of ground cover. Coupled with a prostrate growth habit a particularly good density and ground cover results.

The mean uncut sward height is 35.09 mm, compared with a mean of 30.01 for 'Riley's Super Sport' and 301.63 for 'Greenlees Park'. The mean leaf length (20.83 mm), leaf width (2.31 mm), and mean leaf/width ratio (9.12 mm) shown in Table 1 for 'Plateau' clearly differentiates 'Plateau' from the varieties 'Riley's Super Sport' and 'Greenlees Park'. This combination of characteristics associated with high density and short internode length provides a high density turf of pleasant appearance having excellent ground cover and minimal vertical growth as previously described.

Seed head production of 'Plateau' was low to very low, having a mean number of seed head density (number/100 $cm^2$) of 9.7, compared with a mean seed head density of 12.33 for 'Riley's Super Sport' and 3.83 for 'Greenlees Park'. The low seed head production of 'Plateau' gives an attractive appearance of the turf and decreases the need for mowing to remove seed heads. Where seed heads are allowed to produce flowers, the anther color is red/purple (near 74D).

The subject variety has additional characteristics of long spreading stolons (mean width 1.06 mm), strong rhizomiticity (mean width 1.932 mm), medium leaf length (mean 20.83 mm), and narrow leaf width (mean 2.037 mm). These features additionally characterise the new variety from other *Cynodon dactylon* varieties.

The subject variety contains other standard charcteristics of *Cynodon dactylon* varieties which do not distinguish it from, and are common to, other *Cynodon dactylon* varieties, including culm, glume, sheath and lemma.

The new variety 'Plateau' as previously described is a spontaneous mutation of an unnamed common couch grass (*Cynodon dactylon*) growing on the property of the inventor, Peter Brown, as Collaroy Plateau, New South Wales, Australia in 1975. The unnamed parent variety was characterised by upright shoot growth, thick stolons, long internode length, long leaf length and high seed head frequency. 'Plateau' differs from the parent variety by the features of low growing height, prostrate shoot growth, short internode length, narrow stolon to rhizome width ratio and low to very low seed head frequency as described herein. Vegetative propagation of the mutant stolons was first carried out in 1975 and continuous propagation and selection was carried out giving the resultant 'Plateau' variety.

'Plateau' is a turf grass variety of *Cynodon dactylon* having the aforementioned features which distinguish it from the varieties 'Riley's Super Sport' and 'Greenlees Park', and common couch grass varieties described.

TABLE 1

| | 'Plateau' | *'Riley's Super Sport' | *'Greenlees Park' |
|---|---|---|---|
| UNCUT SWARD (mm) | | | |
| Mean | 35.09 | 30.01 | 301.63 |
| std deviation | 1.53 | 1.57 | 13.80 |
| LSD/sig | 2.65 | P ≦ 0.01 | P ≦ 0.01 |
| LEAF LENGTH (mm) | | | |
| Mean | 20.83 | 13.95 | 75.31 |
| std deviation | 2.48 | 2.39 | 6.50 |
| LSD/sig | 1.40 | P ≦ 0.01 | P ≦ 0.01 |
| LEAF WIDTH (mm) | | | |
| Mean | 2.31 | 2.26 | 2.39 |
| std deviation | 0.23 | 0.25 | 0.35 |
| LSD/sig | 0.09 | ns | ns |
| LEAF LENGTH/WIDTH RATIO | | | |
| Mean | 9.12 | 6.24 | 31.81 |
| std deviation | 1.44 | 1.28 | 2.71 |
| LSD/sig | 0.63 | P ≦ 0.01 | P ≦ 0.01 |
| NODE FREQUENCY (number/cm) | | | |
| Mean | 5.03 | 6.60 | 4.30 |
| std deviation | 1.46 | 1.19 | 0.70 |
| LSD/sig | 0.38 | P ≦ 0.01 | P ≦ 0.01 |
| RHIZOME THICKNESS (mm) Measured 1 cm below soil surface | | | |
| Mean | 1.93 | 1.62 | 1.18 |
| std deviation | 0.30 | 0.36 | 0.20 |
| LSD/sig | 0.21 | P ≦ 0.01 | P ≦ 0.01 |
| STOLON THICKNESS (mm) | | | |
| Mean | 1.06 | 1.29 | 1.00 |
| std deviation | 0.17 | 0.25 | 0.29 |
| LSD/sig | 0.17 | P ≦ 0.02 | ns |
| RHIZOME/STOLON THICKNESS RATIO | | | |
| Mean | 1.83 | 1.29 | 1.26 |
| std deviation | 0.33 | 0.33 | 0.45 |
| LSD/sig | 0.26 | P ≦ 0.01 | P ≦ 0.01 |
| SEED HEAD DENSITY (number/100 $cm^2$) | | | |
| Mean | 9.17 | 12.23 | 3.83 |
| std deviation | 1.34 | 1.50 | 0.94 |
| LSD/sig | 3.71 | ns | P ≦ 0.01 |
| SHOOT EMERGENCE ANGLE O° = vertical, 90° = horizontal | | | |
| Mean | 79.96° | 85.00° | 71.04° |
| std deviation | 2.130 | 1.93 | 4.51 |
| LSD/sig | 0.90 | P ≦ 0.01 | P ≦ 0.01 |
| LEAF COLOR (RHS 1995) | 147A | 137A | 137B |
| LATERAL EXTENSION RATE (cm)* Measured twenty one days of planting | | | |
| Mean | 20 | 15.4 | 18.5 |
| std deviation | 7.9 | 5.28 | 4.22 |
| LSD/sig | 3.28 | P ≦ 0.01 | NS |

*Measured on pioneer stolons growing from 100 mm diameter plugs planted on bare ground at 1.5 m intervals. From the centre of each plug the areas was divided into eight equal 45°sectors. The longest stolon in each sector was measured. Four replicate plugs of each grass were planted.

I claim:

1. A new distinct plant of *Cynodon dactylon* plant named 'Plateau', substantially as described and illustrated.

* * * * *

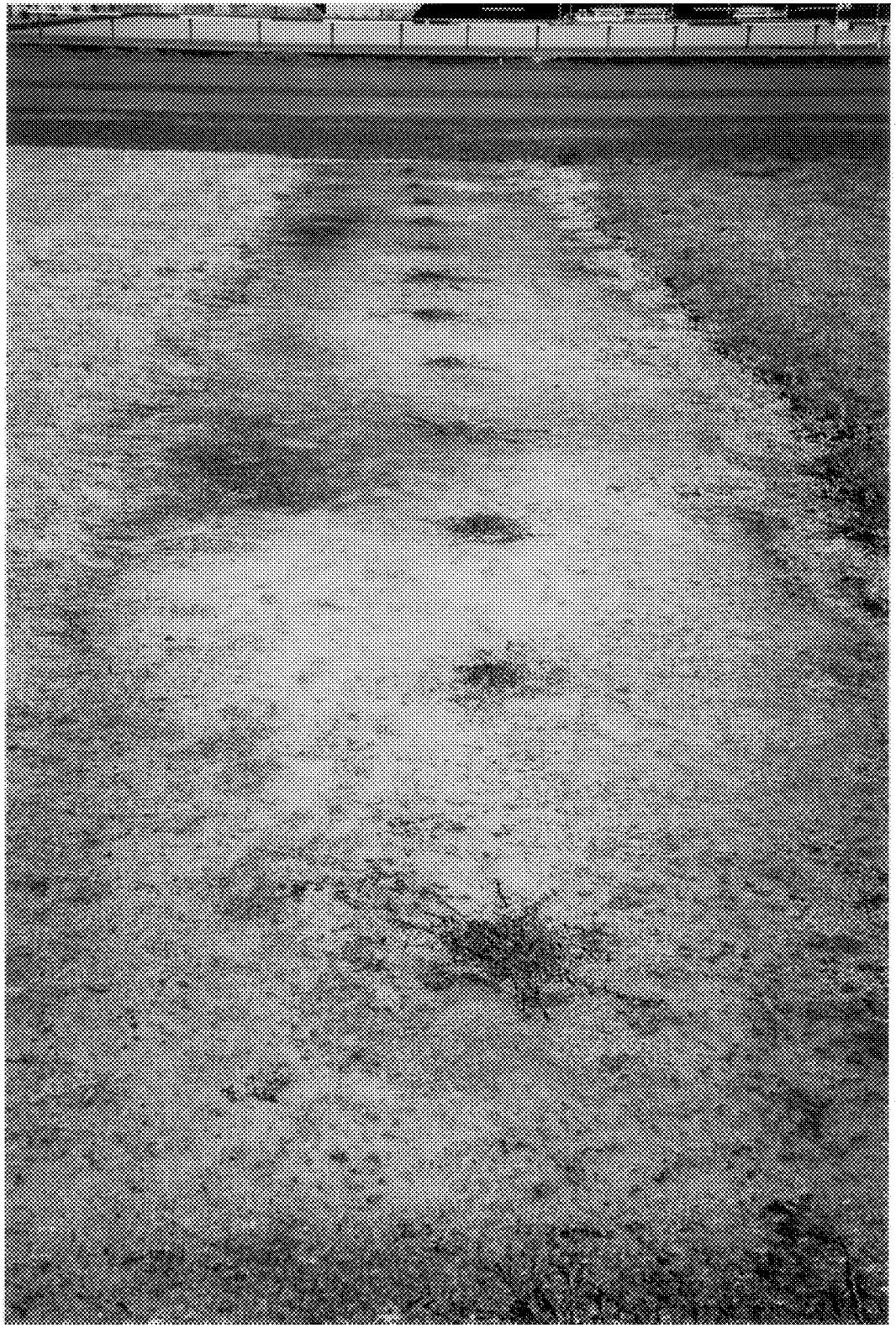

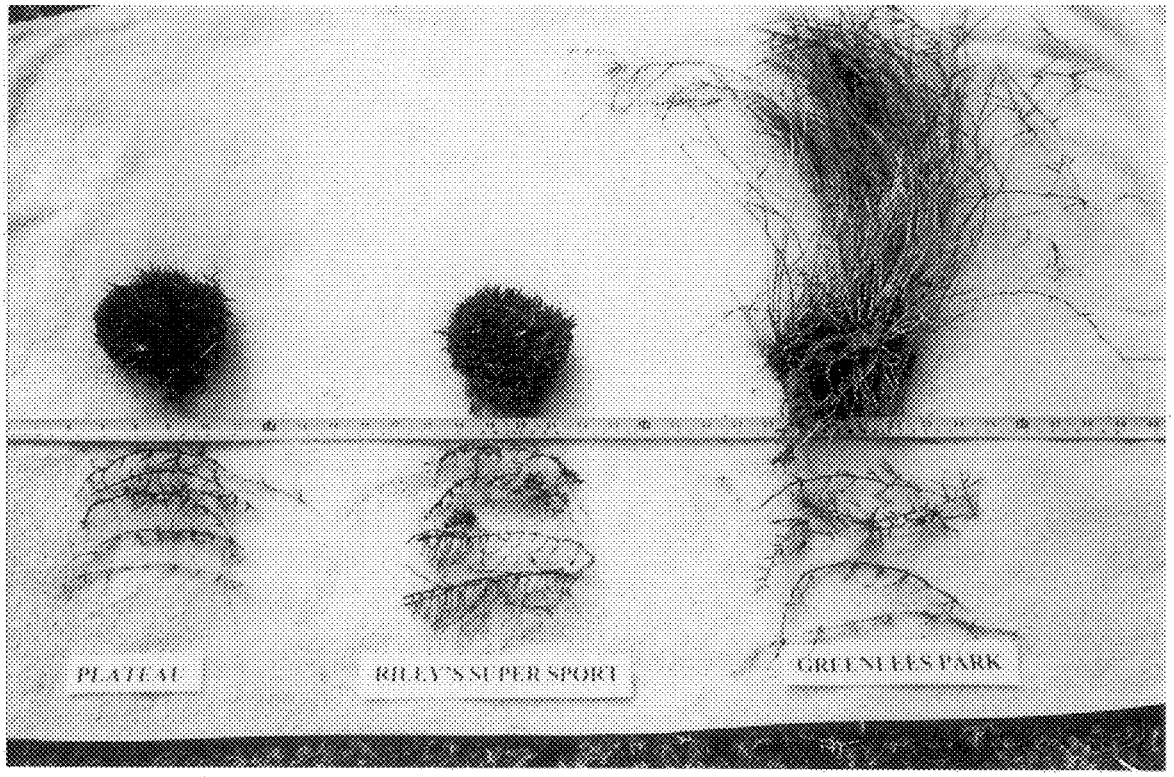
PLATEAU
BILLY'S SUPER SPORT
GREENLEES PARK